(12) United States Patent
Kumar et al.

(10) Patent No.: US 7,414,151 B2
(45) Date of Patent: Aug. 19, 2008

(54) PROCESS FOR MANUFACTURE OF 4-AMINO-HYDROXYBUTYLIDENE-1, 1-BISPHOSPHONIC ACID AND ITS SALTS

(75) Inventors: Ashok Kumar, Maharashtra (IN); Suneel Yeshwant Dike, Maharashtra (IN); Avinash Manohar Nijasure, Maharashtra (IN); Vijaya Bhaware, Maharashtra (IN)

(73) Assignee: IPCA Laboratories Ltd., Mumbai (IN)

( * ) Notice: Subject to any disclaimer, the term of this patent is extended or adjusted under 35 U.S.C. 154(b) by 0 days.

(21) Appl. No.: 11/645,757

(22) Filed: Dec. 27, 2006

(65) Prior Publication Data

US 2007/0149486 A1    Jun. 28, 2007

(30) Foreign Application Priority Data

Dec. 27, 2005    (IN) .................... 1628/MUM/2005

(51) Int. Cl.
    *C07F 9/38* (2006.01)
(52) U.S. Cl. ........................................... 564/15
(58) Field of Classification Search ............. 564/15
    See application file for complete search history.

(56) References Cited

U.S. PATENT DOCUMENTS 4,407,761 A    10/1983    Blum et al.
4,705,651 A    11/1987    Staibano
4,922,007 A    5/1990     Kieczykowski et al.
5,019,651 A    5/1991     Kieczykowski
5,039,819 A    8/1991     Kieczykowski
6,699,850 B2 *  3/2004     Reszka et al. ............ 514/107

FOREIGN PATENT DOCUMENTS

| CN | 1548442 | 11/2004 |
| WO | WO 98/34940 | 8/1998 |
| WO | WO 02/090367 A1 | 11/2002 |

OTHER PUBLICATIONS

Xu, et al, A Facile and Direct Synthesis of Alendronate From Pyrrolidone. OPPI Briefs. 2004, 36, 185-187.*

* cited by examiner

*Primary Examiner*—Kamal Saeed
*Assistant Examiner*—Shawquia Young
(74) *Attorney, Agent, or Firm*—Blank Rome LLP

(57) ABSTRACT

The preset invention relates to a cost effective, high yielding, reproducible method for the manufacture of alendronic acid or its salt, such as sodium alendronate, from inexpensive and readily available pyrrolidone using phosphonating agents such as $PCl_3$ in the presence of acids such as sulphonic acids, sulphuric acid or phosphoric acid, and pharmaceutical dosage forms of alendronic acid or pharmaceutically acceptable salts thereof.

18 Claims, No Drawings

PROCESS FOR MANUFACTURE OF 4-AMINO-HYDROXYBUTYLIDENE-1,1-BISPHOSPHONIC ACID AND ITS SALTS

BACKGROUND OF THE INVENTION

1. Field of the Invention

The present invention relates to a cost effective method for the manufacture of 4-amino-hydroxybutylidene-1,1-bisphosphonic acid (Formula I) and its pharmaceutically acceptable salts, particularly sodium alendronate (Formula II). This invention makes use of a cheaper raw material like pyrrolidone, eliminates the use of phosphorous acid from the phosphonating mixture, and is further characterized by its robustness, simplicity, time cycle reduction, cost effectiveness and environmental friendliness.

2. Background of the Invention 4-amino-hydroxybutylidene-1,1-bisphosphonic acid, also known as Alendronic acid (Formula I), and its sodium salt (Formula II), known as sodium alendronate, is an inhibitor of bone resorption and therefore useful for the treatment of diseases such as Paget's disease, malign hypercalcemia and osteoporosis.

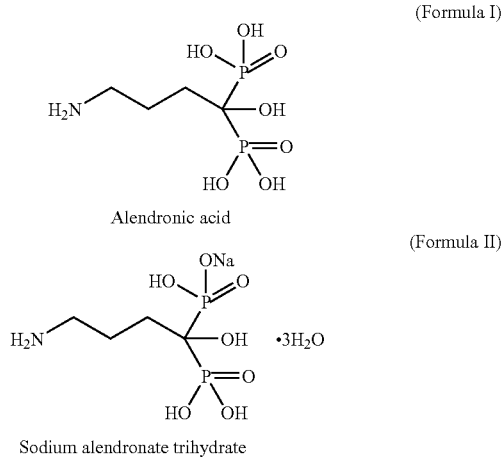

Alendronic acid (Formula I)

Sodium alendronate trihydrate (Formula II)

The preparation of alendronic acid using phosphonation mixture such as $H_3PO_3/PCl_3$, $H_3PO_3/PCl_5$ and $H_3PO_3/POCl_3$ are known in the literature. One such method is described in U.S. Pat. No. 4,407,761 for the preparation of alendronic acid with the above phosphonation mixtures starting from 4-aminobutyric acid (GABA); the reaction product obtained was hydrolyzed under acidic conditions to yield said product.

Another report, disclosed in U.S. Pat. No. 4,705,651, is also found to use the same starting material (GABA) and phosphonation mixture ($H_3PO_3/PCl_3$) but optimizing the ratio of the GABA to $H_3PO_3PCl_3$. However, the problem with the above methods is that, during reaction, local solidification of the mass occurs, which prevents mixing of the components, resulting in incomplete conversion, varying yields and therefore inconsistent outputs being observed. During hydrolysis, hot-spots were created which caused substantial risk in the operation on large scale. The reaction was also attempted in high boiling diluents such as chlorobenzene, but the yields were very poor.

Another improved version, disclosed in U.S. Pat. No. 4,922,007, describes the bisphosphonation of GABA using $H_3PO_3/PCl_3$ in the presence of methane sulphonic acid to make the phoshonation reaction mass homogeneous, thus avoiding local solidification of the reaction mass. However, the hydrolysis of the reaction mass takes longer, perhaps several hours under highly acidic conditions, which became the subject of an improved process disclosed in U.S. Pat. No. 5,019,651. That patent provides an improved hydrolysis step, named as pH controlled hydrolysis, to overcome the problems in the hydrolysis step, for example, formation of a strongly acidic and highly corrosive reaction solution requiring special means, like glass lined vessels, etc., to handle it. However, the reported yield in this improvement is low, which is in the range of 50- to 63-percent based on the starting 4-aminobutyric acid (GABA).

Other reports, as disclosed in WO98/34940 and WO02/090367, disclose the use of diluents like polyethylene glycol, triglycerides of animal or plant oils, respectively, in the phosphonation reaction to solve the problems discussed above. But again, the separation of pure alendronic acid or sodium alendronate from such diluents remains difficult without having multiple purification steps.

Yet another report, U.S. Pat. No. 5,039,819, describes phosphonation of GABA comprising the steps of protecting the amino group with phthalic anhydride, activation of the acid with thionyl chloride, reacting resulting product with an alkylphosphite and finally hydrolyzing the biphosphonic ester obtained, and finally removing the protecting group (phthalimido). However, this method introduces many process steps/operations like protection, deprotection, etc., which are time consuming and generate a lot of effluent and are not desirable for industrial scale operations.

It is evident that most of the methods use similar phosphonation reactions as disclosed in U.S. Pat. No. 4,407,761, making use of phosphonation mixtures such as $H_3PO_3/PCl_3$, $H_3PO_3/PCl_5$ and $H_3PO_3/POCl_3$ and 4-amino-butyric acid material.

An improved method was reported in Chinese Patent No. 1548442A, starting with a much cheaper starting material (compared to 4-aminobutyric acid), pyrrolidone, using 85% methane sulphonic acid and $PCl_3$ as phosphonation reagent. This method appeared to be better, mainly on cost grounds, as the reported yields are better (81-percent). However, actual reproduction of the disclosed process resulted in varying yields and, on carefully optimized conditions, it only yielded 48-percent sodium alendronate.

Therefore, the object of the present invention is to overcome or ameliorate the problems in the prior art such as solidification, hot-spots, uncontrollable exotherms, non-homogeneous reaction conditions, incomplete reaction, etc., and to provide a high yielding and consistent process which can be scaled to industry.

SUMMARY OF THE INVENTION

The above objects are accomplished in the present invention by providing a cost effective, high yielding, reproducible method for the manufacture of alendronic acid or its salt, such as sodium alendronate, from inexpensive and readily available pyrrolidone using phosphonating agents such as $PCl_3$ in the presence of acids such as sulphonic acids, sulphuric acid or phosphoric acid.

Thus, the invention provides a process for making alendronic acid or its salts from pyrrolidone and that includes the steps of (1) treating pyrrolidone with water in the presence of an acid selected from phosphorous chloride, alkyl or aryl sulphonic acid, sulphuric acid, phosphoric acid and their mixtures thereof, characterized by the concentration of water to acid is greater than 25-percent by weight relative to the acid to form a reaction solution; (2) then treating the reaction solution with phosphorous chloride and a diluent followed by hydrolytic reaction to form alendronic acid; and (3) then recovering alendronic acid in free form or as a alkali metal salt.

Among the acids, the preferred acids are methane sulphonic acid and phosphourous chloride. A combination of methane sulphonic acid and phosphorous trichloride is especially preferred.

The diluent is preferably an acid, especially the acids mentioned in step (1) above, such as sulphonic acid, sulphuric acid or phosphoric acid. Methane sulphonic acid is especially preferred for this application. Among the phosphorous chlorides, phosphorous trichloride is preferred.

Thus, the invention also includes a process for making alendronic acid or its salt by a single pot manner without isolation of any intermediates that includes the steps of (1) treating pyrrolidone with phosphorous trichloride or a mixture of phosphorus trichloride and methanesulphonic acid in water, where the concentration of water to acid is greater than 25-percent, until the disappearance of pyrrolidone is observed; (2) adding phosphorous chloride such as $PCl_3$ or $PCl_5$ followed by diluents such as sulphonic acids or sulphuric acid or phosphoric acid; (3) heating the mass at a temperature of about 65 to 85° C. for a period of about 6 to 12 hours; (4) hydrolyzing the resultant product in the reaction under acidic hydrolytic conditions; and (5) isolating the alendronic acid by adjusting the pH to about 1.5 to 2.0 or by adjusting the pH with alkali to about 4.3 to precipitate out sodium alendronate.

In another embodiment of the present invention, the sodium alendronate is prepared without isolation of intermediate 4-aminobutyric acid in a single-pot manner, where the process includes the steps of (1) treating pyrrolidone in water with phosphorus trichloride or its combination with methane sulphonic acid, wherein the concentration of water to acid is greater than 25-percent, until the disappearance of pyrrolidone; (2) removing the excess water (partially or completely) from the reaction mass; (3) adding a further quantity of phosphorous chlorides such as $PCl_3$ or $PCl_5$ followed by diluting the mixture using methane sulfonic acid, or sulphuric acid or phosphoric acid; (4) heating the mass to a temperature of about 65 to 85° C.; (5) hydrolyzing the phosphonation reaction mass under acidic hydrolytic conditions; and (6) isolating sodium alendronate from the reaction mass at a pH of about 4.3.

In accordance with the present invention, the simplicity of the present process is evident from the single-pot conversion and from the elimination of multiple phosphonation reagents in the process, like phosphorous acid. The time cycle for hydrolysis of the pyrrolidone is improved from 9-10 hours to 2-3 hours and the total time cycle from pyrrolidone has been reduced to less than 20 hours from 34-40 hours. The single-pot process is routinely and reliably operated in 5-10 kg batches, affording the higher yield and purity consistently in all batches without any undue process hazards like exotherms, demonstrating the robustness and viability of the process, which makes it available to scale for industrial production. The use of a cheaper raw-material (pyrrolidone) in place of 4-aminobutryic acid, as well as elimination of phosphorous acid from the phosphonation mixture and the one-pot operation, makes the present process cost-effective.

With those and other objects, features, and advantages of the invention that may become hereinafter apparent, the nature of the invention may be more clearly understood by reference to the following detailed description of the invention, the appended claims and to the several drawings attached herein.

DETAILED DESCRIPTION OF THE INVENTION

Although preferred embodiments of the invention are described for illustrative purposes, it should be understood that the invention may be embodied in other forms not specifically described or exemplified.

As used herein, the word "solution" means to cover partial solution or slurry or suspensions or emulsions, etc.

This invention provides an industrial manufacturing method for preparing alendronic acid or its salts, like sodium alendronate, in a single-pot process using inexpensive and readily available pyrrolidone. The present inventive method avoids problems associated with unexpected exotherms, non-homogeneous reaction mass generation, and provides reproducibly high yields while reducing the processing time cycle.

In one aspect, according to the present invention, the process includes treatment of pyrrolidone with water in presence of an acid selected from phosphorous trichloride, alkyl or aryl sulphonic acid, sulphuric acid, or phosphoric acid, and their mixtures thereof, characterized by the concentration of water to the acid is greater than about 25-percent by weight to the acid, until the pyrrolidone is completely hydrolyzed; then mixing it with phosphonylating agent, like phosphorous chloride selected from $PCl_3$ or $PCl_5$ and a diluent; then bringing the mass to a temperature of about 60 to 85° C. for about 6 to 12 hours; and then finally hydrolyzing the phosphonation reaction mixture under acidic hydrolytic conditions and isolating either alendronic acid by adjusting the pH to about 1.5 to 2.0 or sodium alendronate by adjusting the pH to 4.3 from the reaction mass.

Preferably the acid used to treat pyrrolidone is a methane sulphonic acid or phosphorous chloride or a combination of these two acids. Methane sulphonic acid and $PCl_3$ combination is especially preferred.

The diluent is preferably an acid, selected from the group of sulphonic acids, sulphuric acid or phosphoric acid. Sulphonic acids are selected from benzene sulphonic acid or methane sulphonic acid. Among them, methane sulphonic acid is especially preferred.

In the process, according to the invention, the treatment of pyyrolidone with water in the presence of an acid is carried out at a temperature of preferably 100 to 110° C. The molar ratio of pyrrolidone and water can be adjusted in the range of 1.0:6.0 to 1.0:20. It was found that the hydrolysis is completed in about 6 to 7 hours when $PCl_3$ alone is used, while its combination with methane sulphonic acid hydrolyzes pyrrolidone in about 2 to 3 hours.

In the process of the present invention, subsequent to the disappearance of pyrrolidone/complete hydrolysis of pyrrolidone, the mixture is combined with phosphonylating agent $PCl_3$ or $PCl_5$. The reaction mass may be appropriately cooled to avoid any undesired exotherm while incorporation of phosphonating agent $PCl_3$ or $PCl_5$.

A diluent is incorporated into the mixture, the diluent being mineral acid such as methane sulphonic acid or sulphuric acid or phosphoric acid. The combined mixture is heated at a temperature of between about 60 to 85° C. for a period of about 6 to 12 hours. Preferably the phosphonation reagent ($PCl_3$) is added in one lot.

Preferably the total quantity of pyrrolidone to water to $PCl_3/PCl_5$ is in the molar range of 1:6:4 to 1:20:6. The phosphonation reaction is preferably conducted at a temperature of about 70 to 80° C.

The molar ratio of pyrrolidone to phosphorous trichloride used is in the range of about 1.0:4.2 to 1.0:5.3, is especially preferred.

The molar ratio of water to phosphorous trichloride is in the range of about 1.0:0.23 to 1.0:0.70.

After complete phosphonation, the bisphosphonated mass is hydrolyzed by diluting the mass with water and refluxing at a temperature of about 100 to 110° C. for a period of about 3 to 6 hours. On completion of hydrolysis, the pH of the mixture is adjusted to about 4.3 to precipitate the mono sodium alendronate as trihydrate, which is separated from the reaction mass by conventional means, such as filtration or centrifugation, etc.

The sodium alendronate as obtained above may be optionally purified by crystallization from aqueous solvent. Aqueous solvents includes water, or its mixture with water miscible organic solvents such as alcoholic solvents or ketone solvents. The crystallization process involves dissolving crude sodium alendronate in a minimum amount of water, and crystallizing by reducing the temperature. Alternately, the pure sodium alendronate may be precipitated by addition of a second solvent such as alcohol, for example methanol, ethanol, isopropanol, or ketones, such as acetone, etc. The precipitated sodium alendronate may separate from the solvent by conventional means and dried at ambient or higher temperatures at atmospheric or reduced pressure.

In another embodiment according to the present invention, after hydrolytic cleavage of pyrrolidone, the water present in the reaction solution may be removed by conventional means, like distillation prior to the incorporation of a second lot of $PCl_3/PCl_5$ and diluents. Water may be removed at atmospheric pressure or at reduced pressure. Thus, in the process, after complete removal of water, the mass may be diluted with acids such as methane sulphonic acid, sulphuric acid or phosphoric acid followed by addition of further quantity of phosphorous chloride ($PCl_3$ or $PCl_5$). Following this modification, the process can be performed with a reduced quantity of phosphorous chloride as required for completion of the reaction in the previous embodiment. Thus, by following the process of the present invention, the sodium alendronate or alendronic acid can be isolated from the reaction mass without isolation of intermediate 4-aminobutyric acid.

The following examples, which include preferred embodiments, will serve to illustrate the practice of this invention, it being understood that the particulars shown are by way of example and for purpose of illustrative discussion of preferred embodiments of the invention.

EXAMPLE 1

To a 250 ml reaction vessel equipped with a water condenser, 8.5 gm (0.1 mol) pyrrolidone, and 33.5 ml water was added under nitrogen atmosphere. Then, 17.2 gm (0.125 mol) $PCl_3$ was added drop-wise to the mixture while stirring for 20-25 minutes below 65° C., and then it was heated to reflux (i.e., 105 to 110° C.) for 7 hours or until the disappearance of pyrrolidone was observed (monitored by TLC method).

The water from the reaction mass was then distilled off after complete disappearance of pyrrolidone. The mass was then cooled to 60° C. and mixed with 59.24 gm methane sulphonic acid and 41.39 gm (0.3 mol) $PCl_3$ was added drop-wise while maintaining the temperature below 75° C. The reaction mixture was further maintained at 75° C. for 9 hours.

On completion of phosphonation, the reaction mixture was cooled to 40° C., and then 85 ml of water was added and refluxed for 6 hours. The mass was cooled to 70-75° C. and treated with charcoal (0.1 gm) and filtered. The filtrate was adjusted to a pH of 4.3 by mixing with 50-percent sodium hydroxide solution and cooled to 0-5° C. for 8 hours. The precipitated sodium alendronate was filtered off, washed with cold water, and dried under vacuum at 50° C. to produce 26.8 gm of product (yield 82%), having a melting point of between 255 and 258° C.

EXAMPLE 2

In a 250 reaction vessel equipped with a water condenser, 8.5 gm (0.1 mol) pyrrolidone, 14 ml water, and 11.5 gm methane sulphonic acid were added under a nitrogen atmosphere. At room temperature, 17.2 gm (11 ml, 0.125 mol) $PCl_3$ was added drop-wise to the mixture while stirring for 20 to 25 minutes while maintaining the temperature below 65° C. Then, the mixture was heated to reflux (i.e., 105 to 110° C.) for 8 hours or till the disappearance of pyrrolidone was observed (monitored by TLC method).

The mass was then cooled to 60° C. and mixed with 48.13 gm methanesulphonic acid and 55.26 gm $PCl_3$ (0.402 mol) was added drop-wise while maintaining the temperature below 75° C. The reaction mixture was further maintained at 75° C. for 9 hours.

On completion of phosphonation, the reaction mixture was cooled to 40° C., and then 85 ml of water was added and refluxed for 6 hours. The mass was cooled to 70 to 75° C. and treated with charcoal (0.1 gm), and then filtered. The filtrate was adjusted to a pH of 4.3 by mixing it with 50-percent sodium hydroxide solution and cooled to 0-5° C. for 8 hours. The precipitated sodium alendronate was filtered off, washed with cold water, and dried under vacuum at 50° C. to produce 26.4 gm of product (yield 81%), having a melting point of between 255 and 258° C.

EXAMPLE 3

In a reaction vessel, 17.0 g (0.2 mol) pyrrolidone, 22 ml water, and 23 gm methane sulphonic acid were mixed and then heated to reflux (i.e., 105° C.) for 9 hours or till the disappearance of pyrrolidone was observed (monitored by TLC method). The mass was then cooled to room temperature and $PCl_3$ (17.5 ml, 0.199 mol) was added drop-wise while maintaining the temperature below 65° C. The reaction mixture was stirred at 60 to 65° C. for 30 minutes, then the temperature was raised to 110° C. Water was continuously distilled under vacuum. The mass was then cooled to 60° C. A further quantity of 90.39 gm (57.5 ml, 0.6565 mol) $PCl_3$ was then added drop-wise while maintaining the temperature below 60° C., followed by 25.5 ml of $H_3PO_4$ slowly into the mass. Then the reaction mixture was maintained at 75° C. for 9 hours.

On completion of phosphonation, the reaction mixture was cooled to 55° C., and 170 ml of water was added and refluxed for 6 hours. The mass was cooled to 60° C., treated with charcoal (0.1 gm), and then filtered. The filtrate was adjusted to a pH of 4.3 by mixing with 50-percent sodium hydroxide solution and cooled to 0-5° C. for 8 hours. The precipitated sodium alendronate was filtered off, washed with cold water, and dried under vacuum at 50° C., which yielded 39.3 gm of product (yield 61.26%), having a melting point of between 255 and 258° C.

EXAMPLE 4

In a 250 reaction vessel equipped with a water condenser, 8.5 gm (0.1 mol) pyrrolidone, 33.5 ml water, and 11.5 g methane sulphonic acid were added under a nitrogen atmosphere. At room temperature, 17.2 gm (11 ml, 0.125 mol) $PCl_3$ was added drop-wise to the mixture while stirring for 20 to 25 minutes while maintaining the temperature below 65°

C. It was then heated to reflux (i.e., 105 to 110° C.) for 3 hours or until the disappearance of pyrrolidone was observerd (i.e., monitored by TLC method).

The water present in the reaction mass was then removed by distillation. The mass was then cooled to 60° C. and mixed with 48.2 gm methanesulphonic acid and 41.39 gm (0.3 mol) PCl$_3$, which was added drop-wise, while maintaining the exotherm below 75° C. The reaction mixture was further maintained at 75° C. for 9 hours.

On completion of phosphonation, the reaction mixture was cooled to 40° C., and then 85 ml of water was added and refluxed 6 hours. The mass was then cooled to 70 to 75° C., treated with charcoal (0.1 gm), and then filtered. The filtrate was adjusted to a pH of 4.3 by mixing with 50-percent sodium hydroxide solution and cooled to 0-5° C. for 8 hours. The precipitated sodium alendronate was then filtered off, washed with cold water and dried under vacuum at 50° C. to produce 26.4 gm of product (yield 81-percent), having a melting point of between 255 and 258° C.

It will be evident to those skilled in the art that the presently described invention is not limited to the details of the foregoing illustrative examples, and that the present invention may be embodied in other specific forms having other features without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. A process for making alendronic acid or its salts from pyrrolidone comprising the steps of:
   a. treating pyrrolidone with water in the presence of an acid to form a reaction solution, wherein the acid is selected from the group consisting of phosphorous chloride, alkyl or aryl sulphonic acid, sulphuric acid, phosphoric acid, and mixtures thereof, and wherein the concentration of the water to the acid is greater than about 25-percent by weight to the acid;
   b. treating said reaction solution with phosphorous chloride and a diluent, followed by hydrolytic reaction to form alendronic acid; and
   c. recovering alendronic acid in free form or as a alkali metal salt.

2. The process as claimed in claim 1, wherein the process is carried out in a one-pot manner without isolation of intermediates.

3. The process as claimed in claim 1, wherein the diluent is an acid selected from the group consisting of methane sulphonic acid, benzene sulphonic acid, phosphoric acid, and sulphuric acid.

4. The process as claimed in claim 1, wherein the concentration of water to acid is greater than 50-percent weight by weight.

5. The process as claimed in claim 1, wherein the water quantity is greater than 6.0 moles relative to pyrrolidone.

6. The process as claimed in claim 5, wherein the excess water is removed from step (a), before adding diluent or phosphorous chloride.

7. The process as claimed in claim 6, wherein the molar ratio of water to phosphorous trichloride is in the range of about 1.0:0.23 to 1.0:0.70.

8. The process as claimed in claim 7, wherein the molar ratio of pyrrolidone to phosphorous trichloride in step (a) and (b) is in the range of about 1.0:4.2 to 1.0:5.3.

9. The processes as claimed in claim 1, wherein the phosphorous chloride is phosphorous trichloride.

10. The process as claimed in claim 1 wherein step (a) is carried out at a temperature of between about 100 to 110° C.

11. The process as claimed in claim 1, wherein step (b) is carried out at a temperature of between about 60 to 85° C.

12. The process as claimed in claim 1, wherein the diluent is methane sulphonic acid.

13. The process as claimed in claim 1, wherein the acid is a mixture of phosphorous trichloride and methane sulphonic acid.

14. The process as claimed in claim 1, wherein the molar ratio of pyrrolidone to water is in the range of about 1.0:6.0 to 1.0:20.0 relative to pyrrolidone.

15. The process as claimed in claim 1, wherein the recovery of alendronic acid comprises the steps of:
   a. refluxing the reaction solution obtained from step (b) with water;
   b. adjusting the pH of the alendronic acid reaction solution to about 1.5 to 2; and
   c. filtering out the alendronic acid.

16. The process as claimed in claim 1, wherein the recovery of alendronic acid sodium salt comprises the steps of:
   a. refluxing the reaction solution obtained from step (b) with water;
   b. adjusting the pH of the reaction solution to about 4.3; and
   c. filtering out the sodium alendronate trihydrate.

17. The process as claimed in claim 1, further comprising the step of forming a pharmaceutical dosage form, wherein the dosage form comprises the recovered alendronic acid or an alkali metal salt thereof.

18. The process as claimed in claim 17, wherein the dosage form is a tablet.

* * * * *